United States Patent
Wilk

Patent Number: 5,230,705
Date of Patent: Jul. 27, 1993

[54] METHOD OF INTRAVENOUS CATHETERIZATION DEVICE

[76] Inventor: Peter J. Wilk, 185 West End Ave., New York, N.Y. 10023

[21] Appl. No.: 851,097

[22] Filed: Mar. 13, 1992

[51] Int. Cl.$^5$ ............................................. A61M 31/00
[52] U.S. Cl. ...................................... 604/53; 604/104
[58] Field of Search ............... 606/191, 198; 604/164, 604/171, 272, 280, 281, 53, 104, 51

[56] References Cited

U.S. PATENT DOCUMENTS

| | | | |
|---|---|---|---|
| 250,154 | 11/1881 | Master . | |
| 3,788,318 | 1/1974 | Kim et al. . | |
| 4,018,230 | 4/1977 | Ochia et al. . | |
| 4,411,655 | 10/1983 | Schreck | 604/165 |
| 4,449,532 | 5/1984 | Storz | 606/191 |
| 4,480,642 | 11/1984 | Stoy et al. . | |
| 4,581,019 | 4/1986 | Curelaru et al. | 604/164 |
| 4,716,901 | 1/1988 | Jackson et al. | 604/272 X |
| 4,759,748 | 7/1988 | Reed . | |
| 4,827,925 | 5/1989 | Vilasi | 128/207.14 |
| 4,850,975 | 7/1989 | Furukawa | 604/170 |
| 4,862,891 | 9/1989 | Smith | 604/104 X |
| 4,899,729 | 2/1990 | Gill et al. . | |
| 4,919,133 | 4/1990 | Chiang | 606/159 |
| 4,994,070 | 2/1991 | Waters | 606/191 |
| 5,057,083 | 10/1991 | Gellman | 604/164 |
| 5,112,308 | 5/1992 | Olsen et al. | 604/164 |
| 5,139,477 | 8/1992 | Peters . | |
| 5,139,486 | 8/1992 | Moss . | |
| 5,139,511 | 8/1992 | Gill et al. . | |
| 5,158,545 | 10/1992 | Trudell et al. | 604/53 |

*Primary Examiner*—C. Fred Rosenbaum
*Assistant Examiner*—Corrine Maglione
*Attorney, Agent, or Firm*—R. Neil Sudol; Henry D. Coleman

[57] ABSTRACT

A device for use in obtaining intravenous or intraarterial arterial access comprises solid body portion in the form of a cylindrical segment having a pair of longitudinally extending edges, and an elastic membrane connected to the body portion along the edges, whereby the device has a variable transverse cross-section to facilitate the passage of intravenous fluid at a relatively large rate into a vein or artery. The intravenous facilitation device may function as a catheter designed to remain in the vein or artery. Alternatively, the intravenous facilitation device functions as a removable vein dilator through which a catheter is inserted into a vein. In the latter case, the device may further comprise a needle inserted through a channel defined by the solid body portion and the flexible or elastic membrane. In addition, a catheter may be provided in a cylindrical space surrounding the needle and inside the dilating device.

1 Claim, 1 Drawing Sheet

METHOD OF INTRAVENOUS CATHETERIZATION DEVICE

BACKGROUND OF THE INVENTION

This invention relates to an intravenous catheterization device and a related method. In other words, this invention relates to a device for use in obtaining intravenous or intraarterial access. This invention also relates to a catheter and to a method for inserting or deploying a catheter in a vein or artery.

A catherization procedure involves the piercing of a vein or artery with a needle carrying a catheter and subsequently sliding the catheter over the needle and into the punctured blood vessel. After the needle is removed from the catheter, an intravenous tube is connected to the catheter for supplying an intravenous fluid to the patient.

Frequently, a large intravenous flow rate is required in situations where the number or sizes of the accessible veins are severely limited. Consequently, large catheters are inserted into relatively small veins, which results in tears in the veins. Catheters inserted into torn veins fall out. This naturally gives rise to a potentially dangerous circumstance.

In one method for inserting a relatively large catheter into a vein, a small catheter is deployed in a selected vein. Upon the removal of the needle used to pierce the vein, a wire is inserted through the catheter. The catheter is then removed. A vein dilating device having a substantially rigid tapered body is gradually inserted into the vein over the wire, thereby expanding the access opening in the vein. The dilator is subsequently removed and replaced with a large diameter catheter. Finally, the wire is withdrawn from the large catheter.

OBJECTS OF THE INVENTION

An object of the present invention is to provide a method for inserting a relatively large catheter into a vein.

Another, more particular, object of the present invention is to provide such a method which has fewer steps than the above-described wire-facilitated technique.

Another object of the present invention is to provide a device for facilitating the insertion of a relatively large diamter catheter into a vein.

A further particular object of the present invention is to provide such a device which reduces the incidence of torn veins.

Yet another particular object of the present invention is to provide such a device which is easy and inexpensive to manufacture.

SUMMARY OF THE INVENTION

A device for use in obtaining intravenous or intraarterial access comprises, in accordance with the present invention, a solid body portion in the form of a cylindrical segment having a pair of longitudinally extending edges, and an elastic membrane connected to the body portion along the edges, whereby the device has a variable transverse cross-section to facilitate the passage of intravenous fluid at a relatively large rate into a vein or artery.

The intravenous facilitation device may function as a dilating device for assisting in the deployment of an intravenous or intra-arterial catheter. In that case, the device may further comprise a needle inserted through a channel defined by the solid body portion and the flexible or elastic membrane. In addition, a catheter may be provided in a cylindrical space surrounding the needle and inside the dilating device.

Alternatively, the intravenous facilitation device may function as a catheter designed to remain in the vein or artery.

A method for assisting in the deployment of an intravenous or intra-arterial catheter comprises, in accordance with the present invention, the steps of (a) puncturing a blood vessel with a needle, (b) inserting into the blood vessel over the needle a dilating device having a solid body portion and a stretchable membrane portion, (c) inserting a catheter at least partially through the dilating device and partially into the blood vessel, and (d) upon a partial insertion of the catheter into the blood vessel, removing the dilating device from the blood vessel and from around the catheter.

Pursuant to another feature of the present invention, the catheter is inserted into the dilating device subsequently to the removal of the needle therefrom. Alternatively, the catheter may be in the dilating device prior to the puncturing of the vein.

Pursuant to another feature of the present invention, the needle is extracted from the catheter simulataneously with the removal of the vein dilating device from the blood vessel.

A method for inserting a relatively large catheter into a vein, in accordance with the present invention, has fewer steps than the conventional wire-facilitated technique. Accordingly, a method in accordance with the present invention is faster and easier than the other technique.

Use of a device in accordance with the present invention reduces the incidence of torn veins. The effectiveness of the device also saves time in that catheterization procedures need not be repeated as when veins are torn.

A device in accordance with the present invention is easy and inexpensive to manufacture.

DETAILED DESCRIPTION

Figure 1:
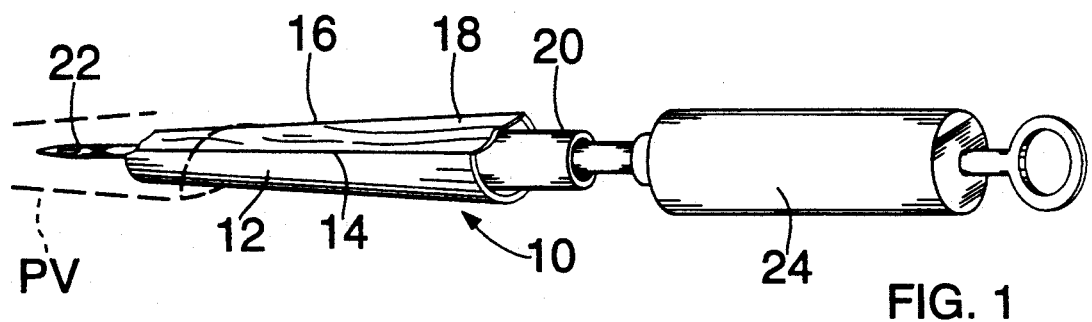
FIG. 1 is a schematic side perspective view of a catheterization assembly in accordance with the present invention.

As illustrated in FIG. 1, an assembly for use in obtaining intravenous or intra-arterial access comprises a dilating device 10 including a solid body portion 12 in the form of a tapered segment having a pair of longitudinally extending edges 14 and 16. Vein dilating device 10 also includes an elastic membrane 18 connected to body portion 12 along edges 14 and 16.

The intravenous or intra-arterial catheterization assembly of FIG. 1 further comprises a relatively large diameter catheter 20 inserted into dilating device or sheath 10. A needle 22 is inserted through catheter 20 and is connected at a proximal end to a hypodermic syringe 24, e.g., for obtaining a blood sample to determine proper intravenous placement.

Membrane 18 provides dilating device 10 with a variable transverse cross-section, whereby the dilating device can be inserted at a relatively small diameter into a patient's vein PV and can expand to facilitate insertion of catheter 20 into vein PV. Dilating device 10 thus facilitates the feeding of intravenous fluid at a relatively large rate into vein PV.

In a method which utilizes the intravenous catheterization assembly of FIG. 1 for assisting in the deployment of intravenous or intra-arterial catheter 20, blood vessel or vein PV is first pierced or punctured by needle 22. Dilating device 10 is then slid over needle 22 into vein PV. Subsequently, catheter 20 is inserted at least partially through dilating device 10 and partially into vein PV. Upon a partial insertion of catheter 20 into vein PV, dilating device 10 is removed from vein PV and from around catheter 20. Simultaneously, needle 22 is extracted from catheter 20.

Figure 2:
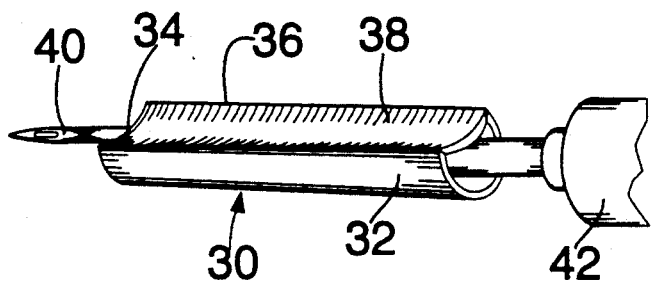
FIG. 2 is a schematic side perspective view of another catheterization assembly in accordance with the present invention.

As illustrated in FIG. 2, another assembly for use in obtaining intravenous or intra-arterial access comprises a dilating device 30 including a solid body portion 32 in the form of a cylindrical segment having a pair of longitudinally extending edges 34 and 36. Vein dilating device 30 also includes an elastic membrane 38 connected to body portion 32 along edges 34 and 36.

The intravenous or intra-arterial catheterization assembly of FIG. 2 further comprises a needle 40 which longitudinally traverses dilating device 20. Needle 40 is coupled at a proximal end to a hypodermic syringe 42.

Membrane 38 provides dilating device 30 with a variable transverse cross-section, whereby the dilating device can be inserted at a relatively small diameter into a patient's vein VV (FIGS. 3A-3C) and can expand to facilitate insertion of a catheter 44 into vein VV. Dilating device 30 thus facilitates the feeding of intravenous fluid at a relatively large rate into vein VV.

Figure 3A:
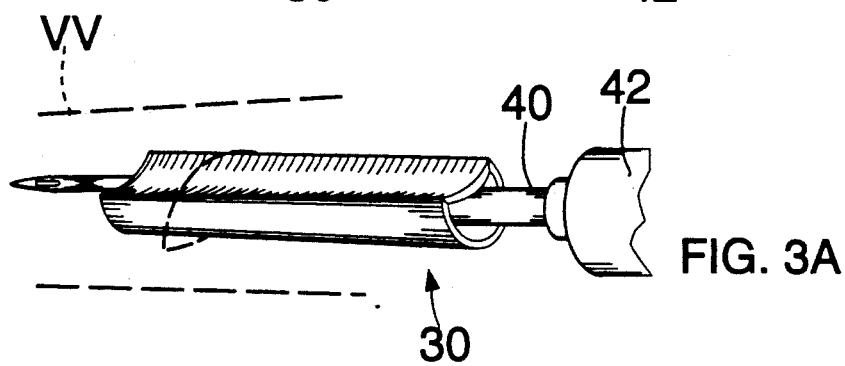
FIGS. 3A-3C are schematic side perspective views of a sequence of steps showing the utilization of the catheterization assembly of FIG. 2 in inserting an intravenous catheter into a vein.
Figure 3B:
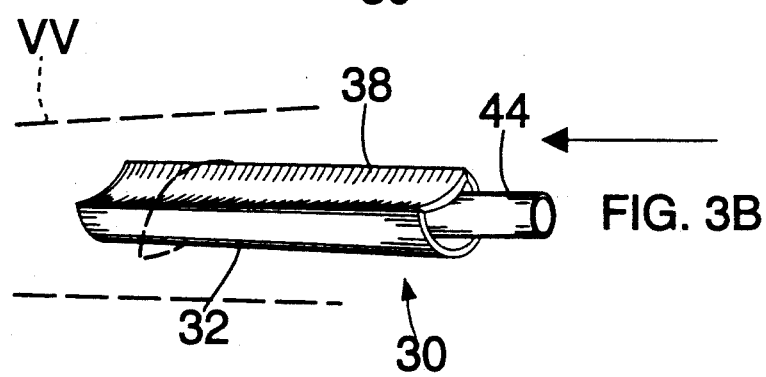
Figure 3C:
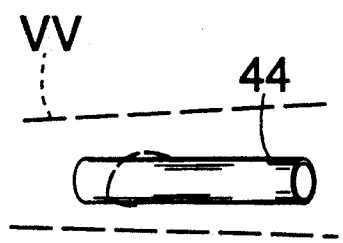

In a method which utilizes the intravenous catheterization assembly of FIG. 2 for assisting in the deployment of intravenous or intra-arterial catheter 44, blood vessel or vein VV is first pierced or punctured by needle 40. Dilating device 30 is then slid over needle 40 into vein VV, as illustrated in FIG. 3A. Subsequently, needle 40 is removed from dilating device 30 and replaced by relatively large diameter catheter 44, as depicted in FIG. 3B. Catheter 44 is inserted at least partially through dilating device 30 and partially into vein VV. Upon a partial insertion of catheter 44 into vein VV, dilating device 30 is removed from vein VV and from around catheter 44 (FIG. 3C).

It is to be noted that intravenous facilitation or vein dilating devices 10 and 30 may alternatively function as catheters designed to remain in vein PV or VV. In that case, the proximal end of the dilating devices 10 and 30 may be provided with coupling elements (not shown) for facilitating the attachment of the dilating devices to intravenous feed tubes.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proferred by way of example to facilitate comprehension of the invention and should not be construed to limit the scope thereof.

What is claimed is:

1. A method for assisting in the deployment of an intravenous or intra-arterial catheter, comprising the steps of:

puncturing a blood vessel with a needle;

inserting into said blood vessel over said needle a dilating device having a solid body portion and a stretchable membrane portion;

removing said needle from said dilating device;

upon removal of said needle from said dilating device, inserting a catheter at least partially through said dilating device and partially into said blood vessel;

stretching said membrane portion and concomitantly expanding said dilating device as a consequence of said step of inserting said catheter; and upon a partial insertion of said catheter into said blood vessel, removing the dilating device from the blood vessel and from around said catheter.

* * * * *